US00PP17144P2

(12) United States Plant Patent
Anatriello

(10) Patent No.: US PP17,144 P2
(45) Date of Patent: Oct. 10, 2006

(54) *CHRYSANTHEMUM* PLANT NAMED 'ATH THREE YTLG'

(50) Latin Name: *Chrysanthemum morifolium*
Varietal Denomination: ATH THREE YTLG

(76) Inventor: Lucilene Anatriello, Rua Cila 3535 Apto 31 CEP: 15015800, San Jose, Do Rio Preto, SP (BR)

( * ) Notice: Subject to any disclaimer, the term of this patent is extended or adjusted under 35 U.S.C. 154(b) by 0 days.

(21) Appl. No.: 11/156,241

(22) Filed: Jun. 17, 2005

(51) Int. Cl.
*A01H 5/00* (2006.01)

(52) U.S. Cl. ..... Plt./295
(58) Field of Classification Search ..... Plt./295
See application file for complete search history.

(56) References Cited

U.S. PATENT DOCUMENTS

PP11,725 P 12/2000 Pieters
PP11,740 P2 1/2001 Boeder
PP14,482 P2 1/2004 Pieters

OTHER PUBLICATIONS

Broertjes, et al. 1980, A mutant of a mutant of a . . . Irradiation of progressive radiation–induced mutants in a mutation breeding programme with *Chrysanthemum morifolium* Euphytica 29: 525–530.*

Gosling, ed. 1979 "The *Chrysanthemum* Manual—6th edition" The National *Chrysanthemum* Society, London, Essex Telegraph Press, Ltd, pp. 329–336.*

Broertjes et al. 1978, "Application of Mutation Breeding Methods in the Improvement of Vegetatively Propagated Crops", Elsevier Sci. Pub. Co., New York, pp. 162–175.*

Searle et al. 1968 "*Chrysanthemum* The Year Round" Blanford Press London pp. 27–29, 320–327.*

* cited by examiner

*Primary Examiner*—Kent Bell
*Assistant Examiner*—Annette H Para
(74) *Attorney, Agent, or Firm*—Knobbe, Martens, Olson & Bear, LLP

(57) ABSTRACT

A new and distinct *Chrysanthemum* plant cultivar is disclosed, characterized by having a yellow-colored daisy type flowers that that bloom prolifically. The plant naturally blooms around the last week of August. The plant is free-branching and flexible, with a very round plant shape.

1 Drawing Sheet

Figure 1:
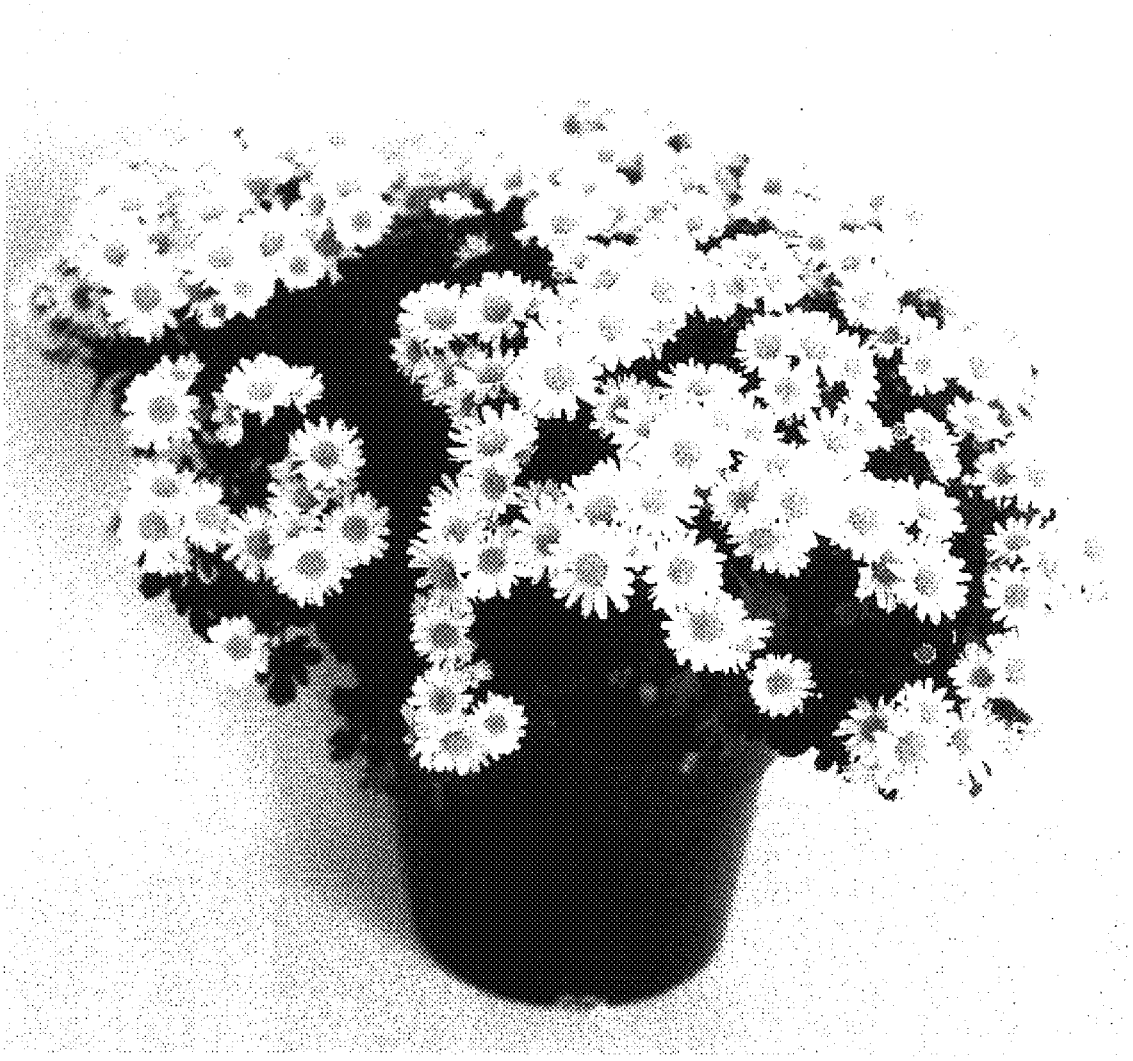

Latin name of the genus and species: *Chrysanthemum morifolium.*
Variety denomination: 'ATH THREE YTLG'.

BACKGROUND OF THE INVENTION

The new cultivar 'ATH THREE YTLG' is a discovered natural mutation of the parent variety 'CGG TNG8' (U.S. Plant Pat. No. 11,740). The new cultivar 'ATH THREE YTLG' was discovered and selected by Lucilene Anatriello in May, 2001, in San Jose Do Rio Preto, State of Sao Paulo, Brazil. The new variety was discovered and selected as a natural mutation which was present on a single branch of the parent variety that was growing in a controlled environment in a plot of approximately 100 plants of the parent variety.

Asexual reproduction of the new cultivar 'ATH THREE YTLG' by terminal cuttings and tissue culture was performed in a controlled environment in Oxnard, Calif. and has shown that the unique features of this cultivar are stable and reproduced true to type on successive generations.

SUMMARY OF THE INVENTION

The cultivar 'ATH THREE YTLG' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ATH THREE YTLG.' These characteristics in combination distinguish 'ATH THREE YTLG' as a new and distinct *Chrysanthemum* cultivar:

1. The new variety has a yellow-colored daisy-type flower.
2. The plant has a very round shape.
3. The new variety flowers prolifically.
4. The plant is free-branching and flexible.
5. The plant has medium vigor.
6. The new variety naturally blooms in the last week of August.

Plants of the new cultivar 'ATH THREE YTLG' are similar to plants of the parent variety, 'CGG TNG8,' in most horticultural characteristics. Plants of the new cultivar 'ATH THREE YTLG' have ray florets that are a different color than the ray florets of the parent variety.

In comparison to the commercially available variety 'GEDI YT8' (U.S. Plant Pat. No. 11,725), 'ATH THREE YTLG' has more ray florets and a flower that lasts approximately nine days longer than the comparable variety. Additionally, the new variety 'ATH THREE YTLG' naturally blooms about three to four weeks earlier than the comparable variety 'GEDI YT8.'

In comparison to the commercially available variety 'GEDI TWO YLATL' (U.S. Plant Pat. No. 14,482), 'ATH THREE YTLG' has more numerous ray florets that are lighter yellow in color. The flower of the new variety 'ATH THREE YTLG' has a larger diameter than the flower of the comparable variety. Further, the new variety 'ATH THREE YTLG' has approximately 13 fewer flowers per stem than the comparable variety 'GEDI TWO YLATL.'

BRIEF DESCRIPTION OF THE PHOTOGRAPH

The accompanying photograph in FIG. 1 illustrates in full color a typical plant of 'ATH THREE YTLG' grown in a 6-inch container. One cutting was used in the pot. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'ATH THREE YTLG' plants grown in a greenhouse in Oxnard, Ventura County, Calif. during the month of September 2003.

The growing temperature ranged from about 12° C. to 15° C. at night to about 12° C. to 20° C. during the day. Measurements and numerical values represent averages of typical flowering types, and are believed to apply to plants of the variety grown under similar conditions of soil and climate elsewhere:

Botanical classification: *Chrysanthemum morifolium* 'ATH THREE YTLG.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 22 cm.
Plant spread: Approximately 28 cm.
Growth rate: Moderate.
Branching characteristics: Free branching.
Length of lateral branches: Approximately 20 cm.
Number of leaves per lateral branch: Approximately 20.
Age of plant described: Approximately 125 days from a rooted cutting.

FOLIAGE

Leaf:
- *Arrangement.*—Alternate.
- *Average length.*—Approximately 6.3 cm.
- *Average width.*—Approximately 5.1 cm.
- *Shape of blade.*—Ovate.
- *Apex.*—Cuspidate.
- *Base.*—Attenuate.
- *Attachment.*—Stalked.
- *Margin.—Palmately lobed and toothed.*
- *Texture of top surface.*—Lightly pubescent.
- *Texture of bottom surface.*—Lightly pubescent.
- *Leaf internode length.*—Approximately 2.4 cm.
- *Color.*—Young foliage upper side: Near Green 137A. Young foliage under side: Near Green 137A. Mature foliage upper side: Near Green 136A. Mature foliage under side: Near Green 136A.
- *Venation.*—Type: Palmately net. Venation color upper side: Near Green 137D. Venation color under side: Near Green 137D.

Petiole:
- *Average length.*—Approximately 1.0 cm.
- *Color.*—Near Green 137D.
- *Diameter.*—Approximately 0.2 cm.

BLOOM

Flower:
- *Flowering habit.*—Induced by darkness period greater than approximately 13.5 hours, approximately 45 days of appropriate day length required to induce and develop blooms.
- *Form.*—Daisy.
- *Natural flowering season.*—Approximately the last week of August and first week of September.
- *Number of flowers per lateral branch.*—Approximately 17.
- *Diameter.*—Approximately 4.8 cm.
- *Disc diameter.*—Approximately 2.1 cm.
- *Depth.*—Approximately 2.0 cm.
- *Longevity on plant.*—Approximately 28 days.
- *Persistence.*—Persistent.

Ray florets:
- *Appearance.*—Matte.
- *Texture.*—Smooth.
- *Average number of ray florets per flower.*—Approximately 50.
- *Shape.*—Oblanceolate.
- *Aspect.*—Flat.
- *Margin.*—Entire.
- *Apex.*—Retuse.
- *Length.*—Approximately 1.3 cm.
- *Width.*—Approximately 1 cm.
- *Color.*—Upper surface at first opening: Near Yellow 4C. Upper surface at maturity: Near Yellow 4B. Upper surface at fading: Near Yellow 3C. Uder surface at first opening: Near Yellow 5C. Uder surface at maturity: Near Yellow 5B. Under surface at fading: Near Yellow 4B.

Disc florets:
- *Appearance.*—Shiny.
- *Texture.*—Smooth.
- *Average number of disc florets per disc.*—Approximately 110.
- *Shape.*—Cylindric.
- *Apex.*—Obtuse.
- *Average length.*—Approximately 0.8 cm.
- *Average width.*—Approximately 0.1 cm.
- *Color.*—At first opening: Near Yellow-green 154B. At maturity: Near Yellow-orange 15C. At fading: Near Yellow-orange 17C.

Peduncle:
- *Length.*—At terminal end (shortest): Approximately 4.1 cm. At lateral end (longest): Approximately 6.4 cm.
- *Angle to stem.*—Acute.
- *Strength.*—Moderate.
- *Color.*—Near Green 137A.
- *Habit.*—Upright.
- *Diameter.*—Approximately 0.2 cm.
- *Surface texture.*—Lightly pubescent.

Flower bud:
- *Length.*—Approximately 0.8 cm.
- *Diameter.*—Approximately 0.8 cm.

*Form.*—Globular.
*Color.*—Near Yellow 3C.

Involucral bracts (phyllaries):
*Appearance.*—Matte.
*Texture.*—Lightly pubescent.
*Number.*—Approximately 35.
*Shape.*—Oblanceolate.
*Margin.*—Entire.
*Apex.*—Acute.
*Length.*—Approximately 0.8 cm.
*Width.*—Approximately 0.8 cm.
*Color.*—Upper side: Near Green 137A. Under side: Near Green 137A.

REPRODUCTIVE ORGANS

Ray florets:
*Number of pistils per floret.*—1.
*Stigma shape.*—2 branched.
*Stigma color.*—Near Yellow 4C.
*Style color.*—Near Yellow-green 154D.
*Style length.*—Approximately 0.7 cm.
*Stamens.*—Absent.

Disc florets:
*Number of pistils per floret.*—1.
*Stigma shape.*—Two-branched.
*Stigma color.*—Near Yellow 2A.
*Style length.*—Approximately 0.2 cm.
*Style color.*—Near Yellow 2D.
*Number of stamens per floret.*—Approximately 5.
*Anther shape.*—Tubular.
*Anther color.*—Near Yellow 11A.
*Pollen color.*—Near Yellow-orange 20A.

OTHER CHARACTERISTICS

Disease resistance: Neither resistance nor susceptibility to diseases or pests has been observed in this variety.

Drought tolerance/cold tolerance: Flowering plants are hardy to a low temperature of about −2° C. Non-flowering plants are hardy in the approximate range of 3° C. to −6° C., depending upon duration of cold an amount of moisture in the soil. With adequate water plants are hardy to a high temperature of 45° C.

Fruit/seed production: Commercially, this plant is not used or observed in a stage wherein seeds would be produced. Therefore, seed production has not been observed.

What is claimed is:

1. A new and distinct cultivar of *Chrysanthemum* plant named 'ATH THREE YTLG' as herein illustrated and described.

* * * * *